United States Patent [19]

Shillington et al.

[11] Patent Number: 5,474,181
[45] Date of Patent: Dec. 12, 1995

[54] NEEDLE REMOVAL AND DISPOSAL APPARATUS

[75] Inventors: Richard A. Shillington, Leucadia; Kenneth R. McCord, Encinitas, both of Calif.

[73] Assignee: Med-Safe Systems, Inc., Oceanside, Calif.

[21] Appl. No.: 413,600

[22] Filed: Mar. 30, 1995

Related U.S. Application Data

[63] Continuation-in-part of Ser. No. 946,523, Sep. 16, 1992, Pat. No. 5,402,887.

[51] Int. Cl.$^6$ ................................................ B65D 83/10
[52] U.S. Cl. ................................. 206/370; 206/366
[58] Field of Search .......................... 206/366, 370; 220/908; 604/192, 198; 29/240

[56] References Cited

U.S. PATENT DOCUMENTS

| | | | |
|---|---|---|---|
| 4,375,849 | 3/1983 | Hanifl | 206/366 |
| 4,466,538 | 8/1984 | Gianni | 206/366 |
| 4,494,652 | 1/1985 | Nelson et al. | 206/370 |
| 4,667,821 | 5/1987 | Shillington | 206/366 |
| 4,738,362 | 4/1988 | Burns et al. | 206/366 |
| 4,842,138 | 6/1989 | Sandel et al. | 206/370 |
| 4,844,245 | 7/1989 | Bennett | 206/366 |
| 4,867,309 | 9/1989 | Germain | 206/366 |
| 4,875,265 | 10/1989 | Yoshida | 29/240 |
| 4,892,191 | 1/1990 | Nakamura | 206/366 |
| 4,955,477 | 9/1990 | Bruno | 206/366 |
| 4,984,686 | 1/1991 | Shillington | 206/366 |
| 4,995,871 | 2/1991 | Sasaki et al. | 604/110 |
| 5,031,767 | 7/1991 | Bruno | 206/370 |
| 5,046,612 | 9/1991 | Mostarda et al. | 206/365 |
| 5,046,613 | 9/1991 | Baudry et al. | 206/366 |
| 5,402,887 | 4/1995 | Shillington | 206/370 |

*Primary Examiner*—David T. Fidei
*Attorney, Agent, or Firm*—Baker, Maxham, Jester & Meador

[57] ABSTRACT

A geared slot needle remover for engaging and rotatably removing a needle from a holder, comprises a support member having an elongated slot for receiving a disposable hypodermic needle, a plurality of gear teeth along one side of the slot for engaging splines on a needle hub for rotating the needle hub and unthreading it from a holder when the gear teeth and the axis of the needle hub are moved transverse to one another, and an elongated lip overlying a substantial length of the slot for engaging and holding the needle hub against removal from the slot. In an alternate embodiment the gear slot is formed in a flexible arm having an inner end secured to the support member, and a needle hub guide for guiding the needle hub along the gear teeth upon movement of the needle holder along the axis of the needle.

17 Claims, 3 Drawing Sheets

NEEDLE REMOVAL AND DISPOSAL APPARATUS

REFERENCE TO RELATED APPLICATION

The present application is a continuation-in-part of application Ser. No. 07/946,523, filed Sep. 16, 1992, now U.S. Pat. No. 5,402,887, entitled "NEEDLE EXTRACTOR FOR DISPOSABLE CONTAINERS".

BACKGROUND OF THE INVENTION

The present invention relates to needle removal devices for syringes, and pertains particularly to an improved needle removal device for quick and easy removal of needles from syringes.

The safe and efficient removal of sharps such as hypodermic needles and the like is a tremendous problem for medical and other healthcare facilities. Needles and syringes are often separated for disposal and sometimes for re-use of the syringe. This is particularly true for blood collection-type syringes which use a vacuum tube for drawing the blood. It is critical that medical personnel have means for removal and disposal of needles without risk of puncture of the skin.

Disposable containers have been developed in recent years which provide a reasonably high degree of security for disposable sharps articles and materials from hospitals and clinics. Many of these articles, such as needles and surgical blades known as sharps, and other similar articles and materials, must be disposed of in a manner to keep them out of the hands of unauthorized persons and to keep them from being reused. These containers are designed to prevent the removal of materials from the container under ordinary circumstances. It is desirable in most instances that the container provide means to remove the needle from syringes and other such instruments prior to disposal or for separate disposal.

One secure container of the aforementioned type is that disclosed in prior U.S. Pat. No. 4,502,606, issued Mar. 5, 1985, and directed to a locking closure for disposable containers. These containers, have usually been provided with needle removal tools in the form of one or more slots which act as a wrench for removal of the needles from syringes and the like. These needle removal tools are not only convenient, but also provide a safe means for removal of the needle. The safe removal of the needle is essential to protect hospital personnel from certain injury and from contagious diseases.

Many prior disposable containers have had needle removal tools built into the top thereof adjacent the disposal opening. This is a convenient and desirable arrangement. However, the prior tools, while normally suitable for most applications, require rotation of the syringe barrel for removal of the needle. This is often inconvenient for the user, particularly if the container must be hand held. An example of an improved needle removal slot is disclosed in my U.S. Pat. No. 4,984,686, granted Jun. 15, 1991.

In the above identified parent application, a needle removal slot is provided which has gear teeth for engaging the splines or flutes of a needle hub for rotatably unthreading the needle. However, further improvements are desirable.

It is, therefore, desirable that an improved, convenient, safe and effective needle removal device be available.

SUMMARY OF THE INVENTION

It is the primary object of the present invention to provide an improved needle removal means for disposable containers.

In accordance with the primary aspect of the present invention, a needle removal device for a disposable container comprises an elongated slot, with a section of gear teeth along one side for engagement with splines on the hub of a needle to rotate and unscrew the needle from its holder as it is passed along the slot transverse to the needle axis. One embodiment includes a flap that engages the needle hub to retain it in the slot. Another embodiment provides the geared slot in a flexible arm that moves transverse to an axially moved needle to unscrew it.

BRIEF DESCRIPTION OF THE PREFERRED EMBODIMENTS

The above and other objects and advantages of the present invention will become apparent from the following description when read in conjunction with the accompanying drawings wherein.

DETAILED DESCRIPTION OF THE PREFERRED EMBODIMENTS

Figure 1:
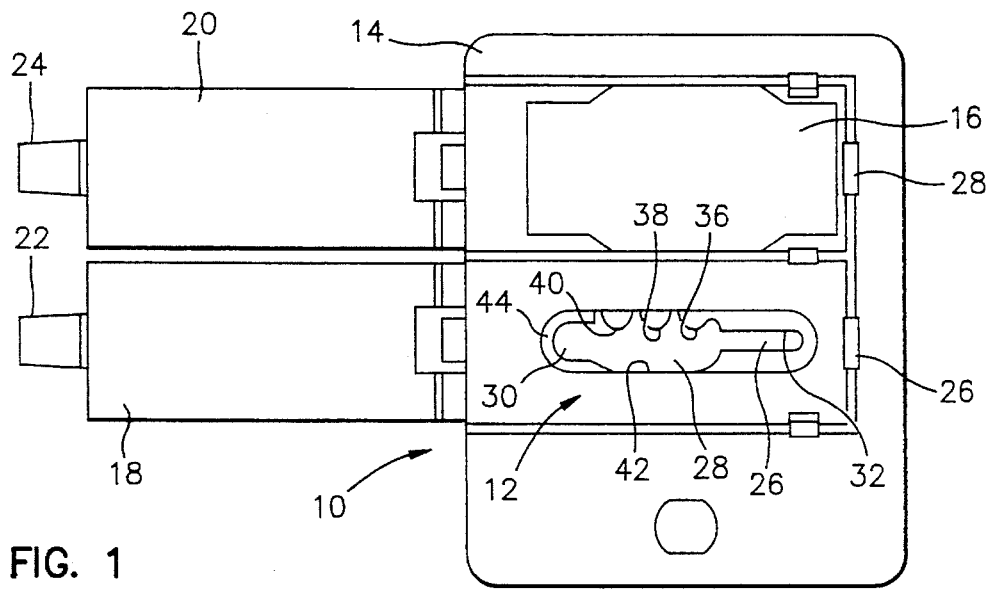
FIG. 1 is a top plan view of a closure assembly incorporating a preferred embodiment of the invention.

Referring now to the drawings and to particularly FIG. 1, there is illustrated a container closure assembly, designated generally by the numeral 10, which includes a needle removal device 12 constructed in accordance with an exemplary embodiment of the invention. This closure assembly comprises a top support or frame member 12, which in the illustrated embodiment has generally rectangular configuration for mounting on and covering the upwardly opening mouth or open top of a container (not shown). This top is permanently attached to a plastic type disposable container of the type typically used for the disposal of syringes, sharps and the like. These type containers are disclosed in a number of my previous patents, as will be mentioned.

The needle removal slot 12 is shown formed in a closure frame 14, which in the illustrated embodiment has a generally rectangular configuration, with an opening 16 for syringes, and covers 18 and 20 for the opening and the needle slot. The needle removal device may also be incorporated into any number of other container closure assemblies associated with various container closures, such as disclosed for example in my U.S. Pat. No. 4,984,686. These tops may be permanently attached to a plastic type disposable container of the type typically used for disposal of sharps, and other objects and the like, such as disclosed in a number of my previous patents.

The illustrated closure assembly is designed for use in conjunction with containers for the disposal of vacuum type syringes widely used for drawing of blood samples. The closure comprises a rectangular panel 14, with an opening 16 for receiving spent syringes. Adjacent to the opening 16 is a removal device in accordance with the invention, designated generally by the numeral 12, for the removal of needles from the syringe body.

The opening 16 and the needle removal slot 12 are positioned within a rectangular recessed portion, as illustrated, with hinged cover members 18 and 20 hinged to one side of the top frame. The hinge covers 18 and 20 are shown pivoted to an open position, and each include locking tabs 22 and 24 for engaging slots 26 and 28 for latching in a permanently latched or closed position when the container is filled and ready for disposal.

Referring now specifically to the needle removal slot, it will be noted that the slot comprises a first or needle receiving portion 26, a second or intermediate and hub receiving portion 28, and an end or needle drop section 30. The overall slot is recessed downward into the closure frame assembly, as will be appreciated from FIGS. 2 and 3. The slot also opens directly into a container for direct disposal of needles.

The needle inlet slot portion 26 slopes downward from the upper surface of frame 14, with opposing parallel side walls 32 and 34 to the intermediate section 28. The intermediate section 28 extends generally horizontally and is formed of a notched wall formed with teeth 36, 38 and 40 and a straight opposing wall 42. The opposing straight wall 42 biases against the hub radial flange and biases the flutes of the hub into engagement with the teeth 36, 38 and 40, causing rotation of the hub and needle as a syringe is held against rotation and passed or moved along the slot transvers to the axis of the needle.

A terminal end of the slot 44 is formed of a continuation of side wall 42, which continues from an upper surface and an opposing side wall above the teeth 36, 38 and 40 and the slot 32. The terminal end portion of the slot extends beneath a generally C or crescent shaped hook or inwardly extending rim 44, which extends over and hooks the radially extending flange of a needle hub for exerting force to force it from the end of a barrel. The teeth 36, 38 and 40 step down slightly from the top surface to the hook 44, permitting a hub flange to extend beneath the hook 44. This also accommodates the unscrewing motion of the hub as it moves downward out of the end of a barrel.

The overall slot 12 is recessed below an upper surface of a support structure, such as a container top, so that there is provided support or spacer surfaces which engage the end of a syringe barrel, and space or position the hub flutes to engage the intermediate portion of the slot and teeth 36, 38, and 40. This is more fully illustrated in the parent application which has been allowed and is incorporated herein in reference as though fully set forth. In particular, as illustrated in the parent application, a syringe barrel shown in phantom has a neck into which a needle hub is threaded. The end surface of the barrel engages the surfaces surrounding or to each side of the slot, and permits the needle hub to extend down just sufficient to engage to gear teeth 36, 38 and 40. In the instant application the barrel end 52a will engage surface 14a surrounding the slot.

Figure 3:
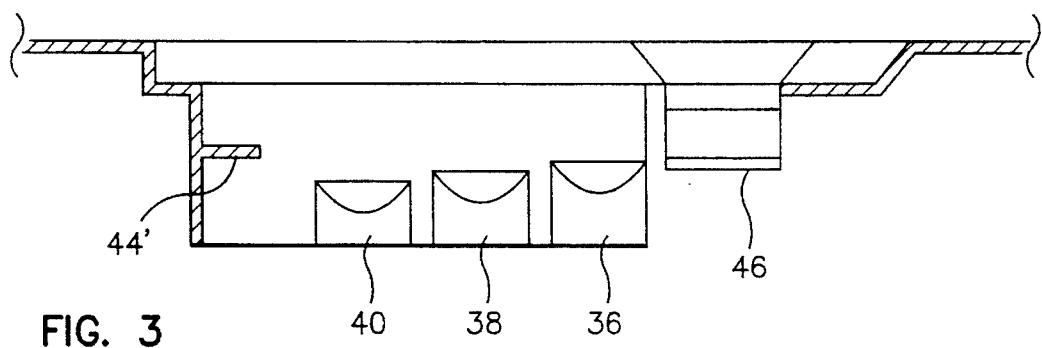
FIG. 3 is a sectional view taken on line 3—3 of FIG. 1.

As the hub unthreads from the end of the barrel, it moves downward as permitted by the downward stepped upper surfaces of the teeth 36, 38 and 40 (e.g. FIG. 3). At the end of the stroke, the flange of the hub extends beneath the horseshoe grip or hook 44 to give an axial force on the needle and hub assembly if needed.

Figure 2:
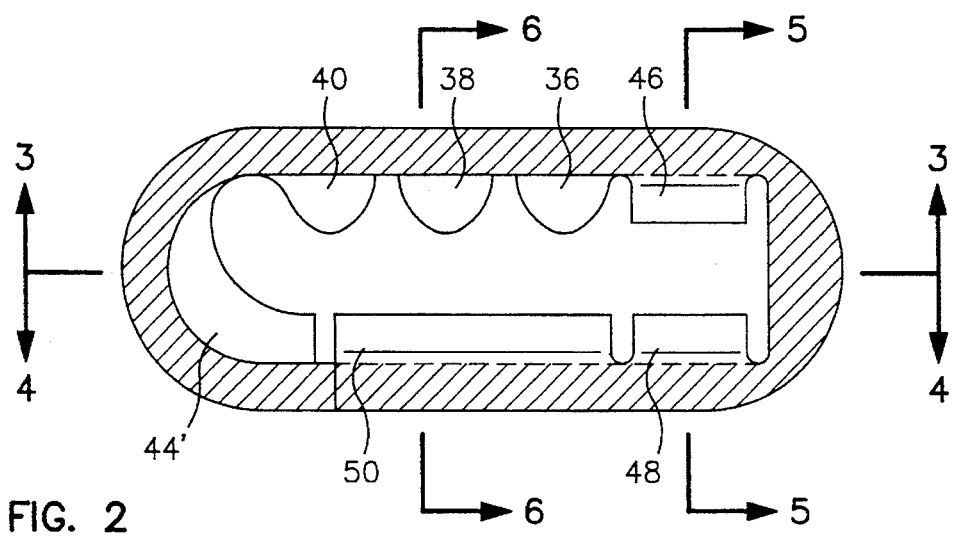
FIG. 2 is a top plan partial view like FIG. 1, showing an alternate embodiment.
Figure 5:
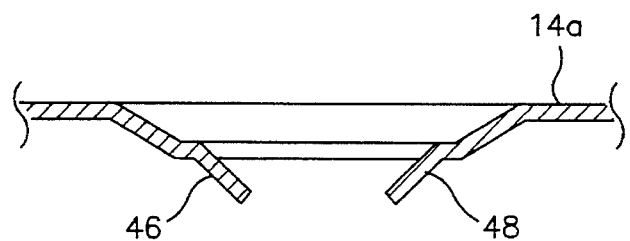
FIG. 5 is a sectional view taken on line 5—5 of FIG. 2.
Figure 6:
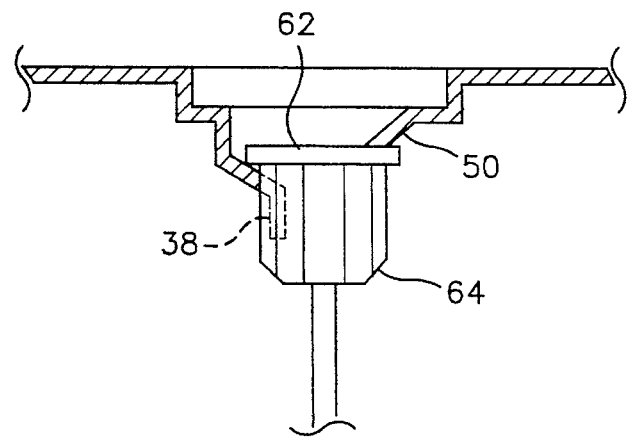
FIG. 6 is a sectional view taken on line 6—6 of FIG. 2.

Referring to FIG. 2 of the drawings, a modification of the basic geared slot of FIG. 1 includes overlying lips or flaps 46 and 48 at the inlet end of the slot 50 and extending along the side of the slot opposite of the gear teeth. These flaps serve as retainers to latch behind the upper surface of the needle hub and retain it in place to prevent it from being pulled out of the slot once inserted. This will be best appreciated in viewing FIG. 4 wherein a conventional needle hub is illustrated, and in FIG. 5 and 6 wherein it can be seen that the flaps will engage behind or above the hub flange and retain it in place. In some instances it may be necessary to campfer the end of the holder neck to provide a space behind the hub rim or flange.

Figure 4:
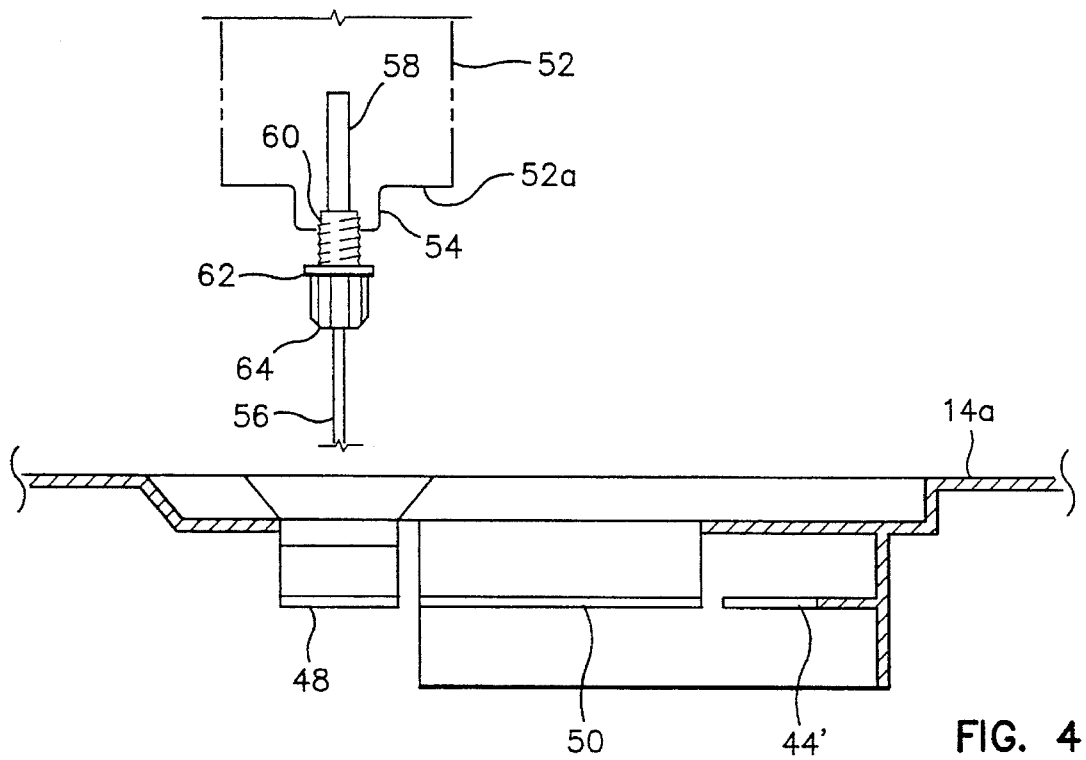
FIG. 4 is a sectional view taken on line 4—4 of FIG. 2.

As specifically illustrated in FIG. 4, a conventional tubular holder or barrel 52 for the vacuum type containers includes a neck 54 having an internally threaded socket for receiving a needle assembly having a forward extending elongated needle 56 and an inwardly extending needle 58 which is covered by a sheath valve and punctures the vacuum tube. A hub assembly includes an upper threaded portion 60, intermediate disk like flange 62 and forwardly extending flutes or splines 64. The threaded portion 60 threading into the internally threaded socket (not shown) in neck 54. The flutes are normally four in number but can serve or act roughly as a pinion gear, which cooperates with the teeth in the slot in a manner similar to a rack gear or linear gear. Thus, the splines on the hub and the gear teeth in the slot act as a rack and pinion gear combination.

In operation, a syringe barrel 62 is grasped in the hand, and the needle 56 is inserted in the inlet to slot 28 and permitted to slide downward, engaging flute 64 in the tooth section of the slot as the barrel is grasped and held against rotation and forced forward along the slot. As the barrel is moved forward along the slot, the flutes 64 engaging the teeth 36, 38 and 40 force the hub to rotate counter clockwise relative to the end of the syringe barrel, forcing the needle hub to unthread or unscrew from the neck 54 of the syringe barrel.

As the needle and hub assembly moves to the terminal end of the slot, the needle and hub assembly is permitted to fall from the end of the barrel. In case it is frictionally held in position, the semicircular grip 46 may be engaged by the hub flange as the barrel is pulled upward, forcing the threaded portion of the needle hub from the end of the barrel neck 54. Thus, the needle is quickly, safely and effectively removed from the end of the syringe barrel.

In the FIGS. 2 through 6 embodiment the syringe barrel is forced downward until the lips or flaps 46 and 48 engage the upper surface of the flange 62 which retains it in place. As the barrel of the syringe is moved forward, lip or flap 52 engages the hub flange 62 as the flutes or splines of the hub engage the tooth 32 and retains it in place as the hub moves forward along the slot. At the end of the slot the flange of the hub extends beneath the hook or rim 44 so that as the barrel 52 is pulled upward the needle hub is engaged and forced out of the end of the barrel.

Figure 7:
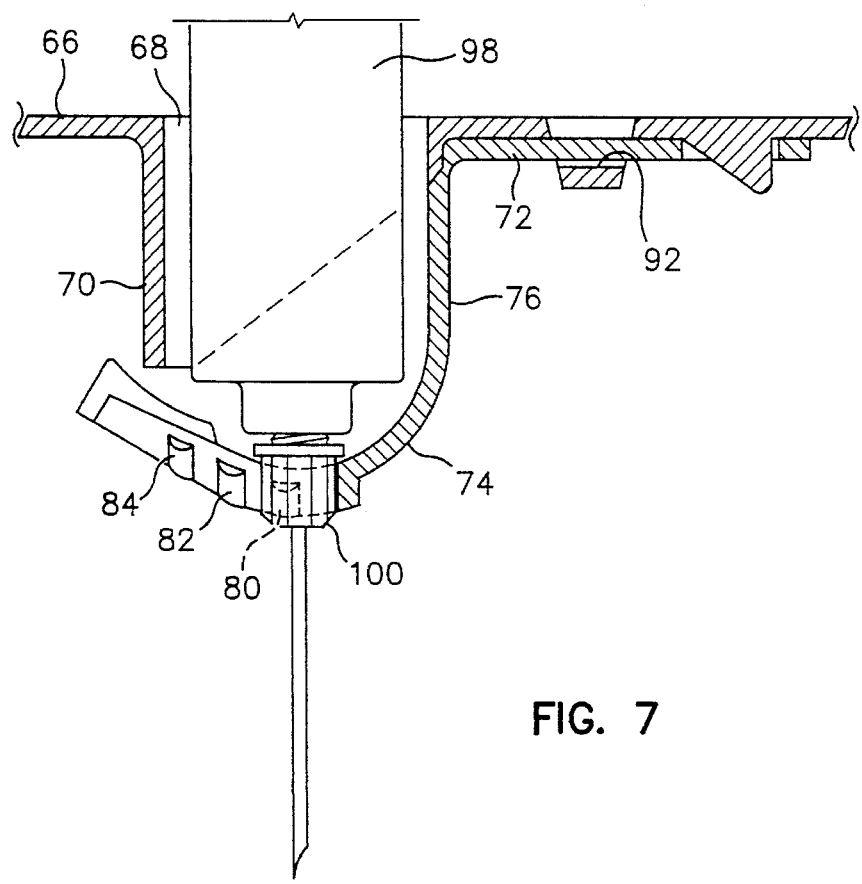
FIG. 7 is a side elevation view in section of a further embodiment of the insertion.
Figure 8:
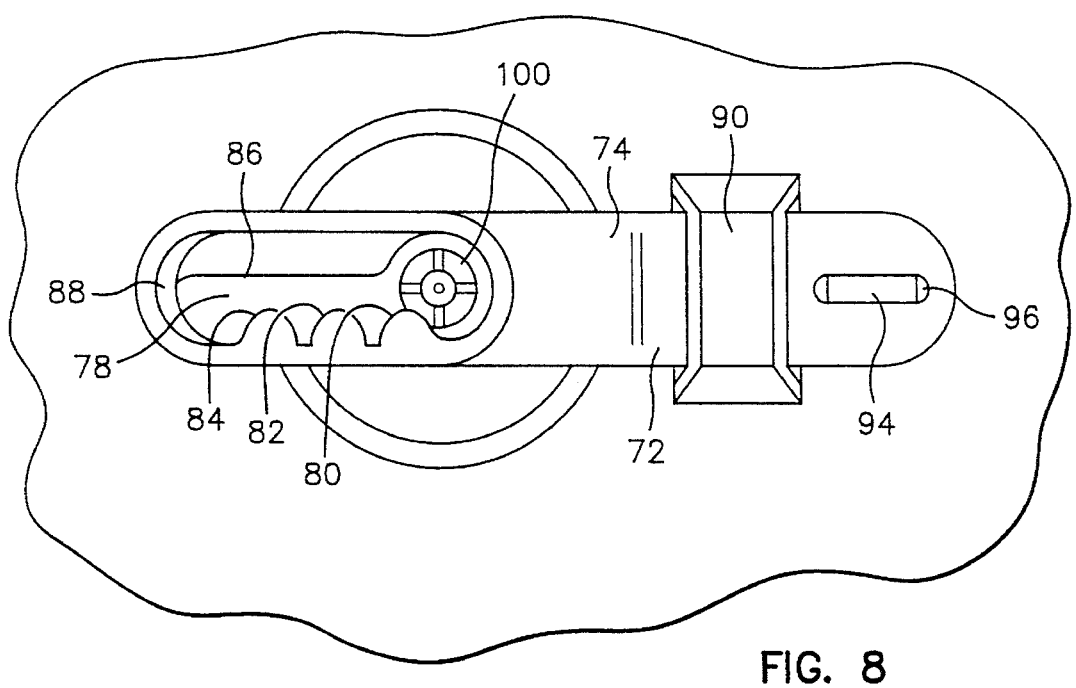
FIG. 8 is a bottom plan view looking upward from below the embodiment of FIG. 7.

Referring now to FIGS. 7 and 8 an alternate embodiment of the invention is illustrated. The device or apparatus of FIGS. 7 and 8 comprises a generally stationary support member 66 which may be a wall or other portion such as a closure assembly of a disposable container. The support member 66 includes an aperture or throughbore 68 which is preferably formed as a tubular sleeve by walls 70 extending normal to the surface of the support member such as into the container. An elongated removal slot assembly is associated with the opening 68 and comprises an elongated flexible arm having an inner end portion 72 for attachment to the surface of the support member 66 and outer flexible arm portion 74 with an intermediate portion 76. The intermediate portion extends at 90° from the base or attachment portion 76 with the flexible end portion 74 at the outer end thereof and including a geared needle removal slot 78. The geared slot 78 includes a plurality of geared teeth 80, 82 and 84 extending along one side thereof and an overlying or opposing lip 86 on the opposite side thereof. A terminal end of the slot includes an overlying hook or rim portion 88 as in the previous embodiment.

The arm assembly may be attached to the support member in any suitable manner such as that illustrated which includes an overlying strap 90 spaced from the undersurface of the wall 66 and forming a slot 92 through which the arm 72 extends and a slot 94 extending and latching into a slot 96 near the end of the strap or arm 72. Thus, the overall slot assembly can be easily mounted by simply slipping the end thereof through the slot 92 and 94 latching into place. The inlet end of the slot is aligned with the axis of the bore 68 to properly position the needle hub at the beginning of the slot.

In operation, as a syringe or needle holder barrel 98 having a needle assembly including a splined hub 100 threadably engaging a socket in a neck 102 is inserted into apparatus or sleeve 68 the splines of the hub 100 extend into the slot as shown in FIG. 8 forward of the series of geared teeth 80 through 84. As the barrel is forced downward along its axis and the arm portion 74 is forced to flex downward and moves to one side pulling the slot portion across the axis of the needle. This moves the gear teeth across the hub and in mesh with the splines forcing the hub to rotate counter-clockwise as it moves downward to the end of the slot 78. This unthreads the needle from its socket whereby it is forced out of the socket and drops into the container or other disposable container. The flexible arm then moves back to the ready position when the holder barrel is removed from the bore.

While the needle slot is illustrated in the present example in conjunction with a specific disposable container top, it is to be understood that it may be utilized in conjunction with substantially any container top, such as disclosed in any number of my prior patents. It may also be used in conjunction with other needle slots, such as shown for example in my U.S. Pat. No. 4,984,684 and others.

While I have illustrated and described my invention by means of specific embodiments, it is to be understood that numerous changes and modifications may be made therein without departing from the spirit and scope of the invention as defined in the appended claims.

We claim:

1. A geared needle remover for engaging and rotatably removing a needle from a holder, comprising:

a stationary support member having an opening for receiving a disposable hypodermic needle;

an elongated slot associated with said opening and having a plurality of gear teeth along one side thereof for engaging splines on a needle hub for rotating the needle hub and unthreading it from a holder when the gear teeth and the axis of the needle are moved transverse to one another; and an elongated lip overlying a substantial length of said slot for engaging and holding the needle hub against removal from the slot.

2. A geared needle remover according to claim 1 wherein said support member includes guide means comprising a generally cylindrical socket for reciprocally receiving a needle receiving end of a needle holder.

3. A geared needle remover according to claim 2 wherein said slot comprises a flexible arm having an inner end secured to said support member, and an outer end including said gear teeth and needle hub guide means for guiding the needle hub along said gear teeth upon movement of the needle holder along the axis of the needle.

4. A geared needle remover according to claim 1 wherein said slot comprises a flexible arm having an inner end secured to said support member, and an outer end including said gear teeth and needle hub guide means for guiding the needle hub along said gear teeth upon movement of the needle holder along the axis of the needle.

5. A geared needle remover according to claim 1 wherein said slot comprises a flexible arm having an inner end secured to said support member, and an outer end including said in-line gear teeth and needle hub guide means for guiding the needle hub along upon movement of the needle holder along the axis of the needle.

6. A geared needle remover according to claim 1 wherein:

said support member is a closure frame for a disposable container; and said guide means comprises a generally cylindrical sleeve for reciprocally receiving a needle receiving end of a needle holder.

7. A geared needle remover according to claim 6 wherein said slot comprises a arm assembly having an inner substantially straight end secured to an under surface of said closure frame, and an outer curved end including said gear teeth.

8. A geared needle remover according to claim 7 wherein said sleeve has a central axis, one end of said slot is aligned with said axis slot comprises a arm assembly having an inner substantially straight end secured to an under surface of said closure frame, and an outer curved end including said gear teeth.

9. A geared needle remover according to claim 7 wherein said sleeve has a central axis, and said outer curved end curves across said axis with one end of said slot aligned with said axis.

10. A geared needle remover for engaging and rotatably removing a needle from a holder, comprising:

a closure frame for a disposable container;

a generally cylindrical opening in said closure frame for receiving a holder for a disposable hypodermic needle;

an elongated slot spaced from and aligned with said opening, said slot having a plurality of gear teeth along one side thereof for engaging splines on a needle hub for rotating the needle hub and unthreading it from a holder when the gear teeth and the axis of the needle are moved transverse to one another.

11. A geared needle remover according to claim 10 wherein said elongated slot includes needle hub guide means for guiding the needle hub along said gear teeth upon movement of the needle holder along the axis of the needle.

12. A geared needle remover according to claim 10 wherein said slot comprises a flexible arm having an inner end secured to said support member, and an outer end including said in-line gear teeth and needle hub guide means for guiding the needle hub along upon movement of the needle holder along the axis of the needle.

13. A geared needle remover according to claim 10 wherein said opening comprises a generally cylindrical sleeve for reciprocally receiving a needle receiving a needle holder.

14. A geared needle remover according to claim 10 wherein said slot comprises an arm assembly having an inner substantially straight end secured to an under surface of said closure frame, and an outer curved end including said gear teeth.

15. A geared needle remover according to claim 14 wherein said sleeve has a central axis, one end of said slot is aligned with said axis slot comprises a arm assembly having an inner substantially straight end secured to an under surface of said closure frame, and an outer curved end including said gear teeth.

16. A geared needle remover according to claim 15 wherein said sleeve has a central axis, and said outer curved end curves across said axis with one end of said slot aligned with said axis.

17. A geared needle remover according to claim 10 wherein said slot includes a retaining flap for overlying and retaining a needle hub in said slot.

* * * * *

UNITED STATES PATENT AND TRADEMARK OFFICE
CERTIFICATE OF CORRECTION

PATENT NO. : 5,474,181
DATED : December 12, 1995
INVENTOR(S) : Shillington et al.

It is certified that error appears in the above-indentified patent and that said Letters Patent is hereby corrected as shown below:

Column 6, line 34, after "axis" delete "slot comprises a arm assembly having an inner substantially straight end secured to an under surface of said closure frame, and an outer curved end including said gear teeth".

Column 7, line 8, after "axis", delete "slot comprises a arm assembly having an inner substantially straight end secured to an under surface of said closure frame, and an outer curved end including said gear teeth".

Signed and Sealed this

First Day of April, 1997

Attest:

BRUCE LEHMAN

Attesting Officer

Commissioner of Patents and Trademarks